United States Patent [19]

Laukonen

[11] Patent Number: 5,093,293

[45] Date of Patent: Mar. 3, 1992

[54] STEAM REACTIVATION OF ZEOLITE CATALYST USED IN PRODUCING PARA-DICHLOROBENZENE

[75] Inventor: Eugene Laukonen, Akron, Ohio

[73] Assignee: PPG Industries, Inc., Pittsburgh, Pa.

[21] Appl. No.: 584,678

[22] Filed: Sep. 19, 1990

Related U.S. Application Data

[62] Division of Ser. No. 373,965, Jun. 30, 1989, Pat. No. 4,990,706.

[51] Int. Cl.$^5$ .............. B01J 29/38; B01J 38/06
[52] U.S. Cl. .................. 502/55; 502/34
[58] Field of Search ............ 502/55, 51, 34, 85

[56] References Cited

U.S. PATENT DOCUMENTS

| | | | |
|---|---|---|---|
| 3,216,789 | 11/1965 | Breck et al. | 23/113 |
| 4,548,914 | 10/1985 | Chu | 502/85 |
| 4,570,023 | 2/1986 | Petruck et al. | 570/210 |
| 4,724,269 | 2/1988 | Suzuki et al. | 570/208 |
| 4,777,305 | 10/1988 | Cobb et al. | 570/208 |
| 4,792,644 | 12/1988 | Hironaka et al. | 570/208 |
| 4,822,933 | 4/1989 | Suzuki et al. | 570/208 |
| 4,835,327 | 5/1989 | Milam et al. | 570/208 |
| 4,849,560 | 7/1989 | Sekizawa et al. | 570/208 |
| 4,194,247 | 4/1990 | Sekizawa | 570/208 |

FOREIGN PATENT DOCUMENTS

| | | | |
|---|---|---|---|
| 0112722 | 7/1984 | European Pat. Off. | 570/208 |
| 0118851 | 9/1984 | European Pat. Off. | 570/208 |
| 0154236 | 9/1985 | European Pat. Off. | 570/206 |
| 0171265 | 2/1986 | European Pat. Off. | 570/208 |
| 038498 | 3/1977 | Japan | 502/55 |
| 56-92227 | 7/1981 | Japan | 570/207 |
| 57-77631 | 5/1982 | Japan | 570/206 |

OTHER PUBLICATIONS

H. F. Wiegandt et al., *Industrial and Engineering Chemistry*, vol. 43, No. 9, pp. 2167–2172 (1951).

L. Wilkosz, *Przemys Chemiczny*, vol. 51, No. 8, pp. 524–527 (1972).

D. W. Breck, *Zeolite Molecular Sieves*, pp. 156, 177, 361, 369 (1974).

Kirk–Othmer, *Encyclopedia of Chemical Technology*, 3rd Ed., vol. 5, pp. 797–808, 819–827 (1979).

T. Huizinga et al., *Tetrahedron Letters*, vol. 21, pp. 3809–3812 (1980).

M. Windholz, *The Merck Index*, 10th Ed., p. 1454 (1983).

*Primary Examiner*—Paul E. Konopka
*Attorney, Agent, or Firm*—George D. Morris

[57] ABSTRACT

As zeolite L is used as catalyst for the chlorination of benzene, chlorobenzene, ortho-dichlorobenzene, and/or meta-dichlorobenzene, its catalytic activity diminishes. Zeolite L which has been used for such chlorinations may be reactivated by contact with steam.

12 Claims, No Drawings

STEAM REACTIVATION OF ZEOLITE CATALYST USED IN PRODUCING PARA-DICHLOROBENZENE

This is a divisional of application Ser. No. 07/373,965, filed June 30, 1989, now U.S. Pat. No. 4,990,706.

BACKGROUND OF THE INVENTION

Para-dichlorobenzene is frequently produced by chlorinating benzene and/or chlorobenzene. The formation of para-dichlorobenzene is accompanied by the formation of various by-products such as ortho-dichlorobenzene, meta-dichlorobenzene, more highly chlorinated benzenes, and often some degradation products. In many instances once the desired amount of para-dichlorobenzene (usually, but not necessarily close to the maximum yield attainable) has been produced, the chlorination is terminated in order to conserve chlorinating agent and to maintain the production of undesirable higher chlorinated benzenes at acceptably low levels. It is usually found in these situations that the principal by-product is ortho-dichlorobenzene.

One known way to favor the production of para-dichlorobenzene while reducing the coproduction of the less desired ortho-dichlorobenzene, is to conduct the chlorination in the presence of a catalytic amount of zeolite L catalyst. Such chlorinations are discussed in U.S. Pat. Nos. 4,724,269 and 4,777,305; in European Patent Application Publications No. 0 118 851, 0 154 236, and 0 171 265; and in Huizinga et al, *Tetrahedron Letters*, Volume 21, pages 3809-3812 (1980), the disclosures of which are, in their entireties, incorporated herein by reference, including especially their descriptions of zeolite L catalysts, the making of such catalysts, and the use of such catalysts in the chlorination of benzene and/or chlorobenzene. U.S. Pat. No. 3,216,789 discloses zeolite L, its preparation and characteristics. D. W. Breck, *Zeolite Molecular Sieves*, pages 156 and 361, and L. Wilkosz, *Przemys Chemiczny*, Volume 51, No. 8, pages 524-527 (1972) discuss zeolite L and its characteristics. The disclosures of U.S. Pat. No. 3,216,789 and the cited pages of the Breck and Wilkosz publications are, in their entireties, incorporated herein by reference.

A convenient ratio for characterizing the relative proportions of para-dichlorobenzene and ortho-dichlorobenzene in the organic feedstock, in organic intermediates, and in the organic reaction product is the "para/ortho ratio", often abbreviated as "P/O" or "P/O ratio", which is the ratio obtained by dividing the moles of para-dichlorobenzene present by the moles of ortho-dichlorobenzene present. Sometimes the "ortho/para ratio", often abbreviated as "O/P" or as "O/P ratio", which is the inverse of the P/O ratio, is used for characterization purposes.

While the P/O ratio is useful for monitoring relative proportions of para-dichlorobenzene and ortho-dichlorobenzene, it provides little or no information as to how far the chlorination has progressed. A convenient scale of reference which provides this information is the "x-value" which reflects the degree of chlorination of the benzene-based compounds in the organic feedstock, in organic intermediates as the reaction progresses, and in the organic reaction product. The x-value is the value of x in the empirical formula for a mixture of such compounds: $C_6H_{6-x}Cl_x$. It may be calculated as follows:

$$x\text{-value} = \frac{B + 2C + 3D + 4E + 5F + 6G}{A + B + C + D + E + F + G}$$

where
A = moles of benzene present;
B = moles of monochlorobenzene present;
C = moles of dichlorobenzene (all isomers) present;
D = moles of trichlorobenzene (all isomers) present;
E = moles of tetrachlorobenzene (all isomers) present;
F = moles of pentachlorobenzene present; and
G = moles of hexachlorobenzene present.

The x-value of the organic reaction product is greater than that of the organic feedstock.

Although zeolite L favors high P/O ratios for organic intermediates and organic reaction products, its effectiveness in this regard declines with continued use. Thus under substantially similar reaction conditions using substantially similar organic feedstocks, the P/O ratio at a given x-value is often lower for later chlorinations than it is for earlier chlorinations using the same zeolite L catalyst. Eventually the catalytic effectiveness of the zeolite L becomes nil.

THE INVENTION

It has now been found that zeolite L which has previously been used as catalyst for the catalytic chlorination of benzene and/or chlorobenzene may be substantially reactivated by treatment with steam. While under substantially similar operating conditions the P/O ratio declines with continued use of the zeolite L catalyst, whether steam-treated or untreated, the steam treatment does permit acceptably high P/O ratios to be reestablished, thereby prolonging the useful life of the catalyst.

It has also been most surprisingly found that steam-treatment of virgin zeolite L catalyst, that is, zeolite L catalyst that has not previously been used for chlorination reactions, often permits higher P/O ratios to be obtained early in the catalyst lifetime than when it is not steam-treated. The reasons for this are not understood.

The above discussion has placed emphasis on the P/O ratio of the final organic reaction product where the chlorination has been terminated so that the principal coproduced by-product is ortho-dichlorobenzene. In some circumstances, however, it is desirable to permit the chlorination reaction to continue in order to convert all or a portion of the coproduced ortho-dichlorobenzene (and meta-dichlorobenzene, if any is present) to higher chlorinated benzenes. Since the presence of a catalytic amount of zeolite L during the chlorination of ortho-dichlorobenzene and/or meta-dichlorobenzene favors the formation of 1,2,4-trichlorobenzene vis-a-vis the other trichlorobenzene isomers, continued chlorination of benzene and/or chlorobenzene is sometimes desirable when coproduced 1,2,4-trichlorobenzene is more desirable than coproduced ortho-dichlorobenzene. The para-dichlorobenzene produced in the earlier stages of chlorination remains largely unaffected during the continued chlorination, and so the P/O ratio increases as the ortho-dichlorobenzene is consumed. Thus, the use of steam treated zeolite L as catalyst is particularly beneficial where it is desired to at least approximately maximize the production of para-dichlorobenzene as the principal product while obtaining 1,2,4-trichlorobenzene as the principal by-product.

Accordingly, one embodiment of the invention is a process for reactivating zeolite L which has previously been used as catalyst for the catalytic chlorination of benzene, chlorobenzene, or a mixture thereof, the process comprising contacting the zeolite L with steam.

Another embodiment of the invention is a process comprising reacting benzene, chlorobenzene, or a mixture thereof initially present in an organic feedstock with chlorinating agent in the presence of reactivated zeolite L to produce an organic reaction product having an x-value greater than that of the organic feedstock, wherein the reactivated zeolite L is zeolite L which has previously been used as catalyst for the catalytic chlorination of benzene, chlorobenzene, or a mixture thereof and which has thereafter been contacted with steam.

Zeolite L is a known crystalline zeolite as discussed above. Zeolite L contains exchangeable cations. The cations in any particular crystal of zeolite L may be essentially the same or they may be different and in varying proportions. In general, the exchangeable cations are metal cations or cations, as for example, hydrogen and ammonium, which behave like metal cations in that they may be replaced for other exchangeable cations without causing a substantial alteration of the basic crystal structure of the zeolite. Most often the exchangeable metal cations are monovalent, divalent, or trivalent, particularly those of Groups I, II and III of the Periodic Table. Cations of many of the transition metals, lanthanides, and actinides may be used when desired. In the present invention, the exchangeable cations most commonly employed in the zeolite L are sodium, potassium, calcium and/or hydrogen, although other cations may be used when desired. Potassium zeolite L, in which most of the exchangeable cations are potassium cations, is preferred for use in the present invention.

The organic feedstock for the reaction comprises benzene, chlorobenzene, or a mixture thereof. Other compounds may also be present. In most cases the feedstock comprises at least about 10 percent by weight benzene, chlorobenzene, or a mixture thereof. Frequently the organic feedstock comprises at least about 50 percent by weight benzene, chlorobenzene, or a mixture thereof. At least about 90 percent by weight of one of more of these compounds is preferred.

The chlorination reaction is generally conducted in a reaction medium comprising a liquid phase and a catalytic amount of the reactivated zeolite L (nominally referred to as a "liquid phase reaction"). The reaction however may be conducted in a reaction medium consisting of a gas phase and a catalytic amount of the reactivated zeolite L (nominally referred to as a "gas phase reaction").

The reaction may be conducted batchwise, continuously, semi-batchwise, or semi-continuously. Continuous reactions in which chlorinating agent and feedstock are continuously introduced to a reactor containing the reactivated zeolite L and in which reaction product is continuously removed from the reactor, are preferred. Semi-batchwise reactions, especially those in which chlorinating agent is added continuously or intermittently to a batch of the feedstock, are often employed. Semi-continuous reactions in which one of the reactants is added continuously to a reactor containing the reactivated zeolite L while the other reactant is added intermittently, may be used. Strictly batchwise reactions are usually employed only when the chlorinating agent either produces molecular chlorine slowly or reacts slowly with benzene, chlorobenzene, or a mixture thereof under the conditions of the reaction. The reaction may be conducted in the presence of extrinsic diluent or no extrinsic diluent may be used. In the semi-batchwise reaction method, the weight ratio of reactivated zeolite L to the benzene, chlorobenzene, or a mixture thereof initially present may vary widely. In most cases, however, the weight ratio is in the range of from about 0.1:100 to about 20:100. Often the weight ratio is in the range from about 1:100 to about 15:100. A weight ratio in the range of from about 2:100 to about 10:100 is preferred.

Irrespective of the type of reaction, the chlorinating agent may be any material which will chlorinate, either directly or indirectly, benzene, chlorobenzene, or a mixture thereof. The chlorination agents themselves are well known. Examples of chlorinating agents include molecular chlorine, sulfuryl chloride, sulfur monochloride, N-chlorosuccinimide, phosphorous pentachloride, and chloride monoxide. The preferred chlorinating agent is molecular chlorine.

In many cases only a portion of the chlorine content of the chlorinating agent is available for the desired chlorination. This may be due to a variety of causes. Undesired side reactions, for example, may sometimes consume a portion of the chlorine. Often, the nature of the reaction itself is such that, even ideally, only a portion of the chlorine content of the chlorinating agent is available for chlorination. As an example of the latter situation, the reaction of one mole of elemental molecular chlorine with one mole of chlorobenzene results in the evolution of one mole of hydrogen chloride. The evolved hydrogen chloride is often recovered and used to produce other useful materials. It may be seen that the availability of chlorine atoms for desired chlorination is a factor to be considered in choosing relative proportions of the chlorinating agent and the feedstock to be used in conducting the reaction. Other factors to be considered include the x-value of the feedstock and the x-value to be achieved in the organic reaction product. In general, sufficient chlorinating agent should be introduced to the reaction to accomplish the desired degree of chlorination of the feedstock.

The temperatures at which the reaction is conducted are similarly subject to wide variation but ordinarily they are in the range of from about 40° C. to about 200° C. In many cases the temperatures are in the range of from about 70° C. to about 130° C. From about 90° C. to about 110° C. is preferred.

The pressures at which the reaction is conducted may also be varied widely. Ambient atmospheric pressure or slightly higher is generally employed although greater or lesser pressures may be used. In most cases, the pressure is in the range of from about 0 to 700 kilopascals, gauge. Frequently, the pressure is in the range of from about 0 to about 350 kilopascals, gauge.

The para-dichlorobenzene and the various by-products may be recovered from the organic reaction product by any of the various techniques known to the art.

The steam used to contact the zeolite L during reactivation may be wet saturated steam, dry saturated steam, or superheated steam.

The pressure of the steam with which the zeolite L is contacted may vary widely, but usually it is in the range of from about 0 to about 1500 kilopascals, gauge. Generally the steam pressure is above ambient atmospheric pressure. In most cases, the steam pressure is at least about 130 kilopascals, gauge. Often the steam pressure is in the range of from about 130 to about 1100 kilopascals, gauge. From about 480 to about 690 kilopascals, gauge, is preferred.

The temperature of the steam with which the zeolite L is contacted may also vary widely. In most cases the temperature of the steam is in the range of from about 100° C. to about 300° C., although higher temperatures which do not substantially adversely affect the zeolite L or its performance may be used. Frequently the temperature is in the range of from about 100° C. to about 200° C. Temperatures in the range of from about 150° C. to about 170° C. are preferred.

The time for which the zeolite L catalyst is contacted with steam may vary widely and depends upon such factors as the steam pressure, the amount of catalyst being steam treated, catalyst history (the period for which it was used since the last steam treatment, the conditions of the previous steam treatment, the number and length of previous cycles of use and steam treatment, etc.), and the manner in which the catalyst is contacted with the steam. The minimum time of steam treatment is low since steam treatment for even a minimal time would be expected to accomplish at least a minimal improvement in subsequent catalyst performance. The maximum time is not limited by theory but by practical convenience. When desired, thermogravimetric analysis and/or X-ray analysis may be used to ascertain the point where maximum removal of heavies has been achieved, and hence the point where regeneration has been completed. Usually the zeolite L catalyst is contacted with steam for at least about one hour. Frequently it is contacted with steam for at least about 3 hours. In many cases the period for which the zeolite L catalyst is contacted with steam is in the range of from about 1 hour to about 48 hours. Often the period is in the range of from about 3 to about 24 hours. Preferably the period is in the range of from about 5 to about 12 hours. The time period of steam treatment may be for a single, continuous steam treatment or it may be the sum of intermittent periods of steam treatment.

While the steam may be simply injected into a container containing the zeolite catalyst in the absence of a vapor purge from the container, it is preferred to pass steam through the catalyst since this manner of steam treatment is more effective in reactivating the catalyst.

Upon completion of the steam treatment the zeolite L catalyst is preferably substantially dried. Although damp or somewhat wet zeolite L catalyst may be used in the chlorination of benzene and/or chlorobenzenes, this mode of operation is not preferred since hydrogen chloride in the presence of sizable amounts of water or water vapor is often corrosive to equipment. Zeolite L catalyst saturated with water is inactive.

Drying may be accomplished by a wide variety of techniques which are themselves known to the art. Although drying is usually accomplished at about ambient atmospheric pressure, lower or higher pressures may be used as desired. Similarly, ambient temperatures may be employed or higher temperatures may be used to accelerate water and/or water vapor removal. Temperatures in the range of from about 90° C. to about 200° C. are especially useful. A purge of a substantially nonreactive gas (such as nitrogen, argon, helium, etc.) may be used when desired. The drying time may vary widely. Preferably the steam treated zeolite L catalyst is substantially dried such that any water or water vapor remaining (if any) is trivial or inconsequential to the subsequent chlorination reaction. Drying times in the range of from about 1 to 24 hours are frequently employed. From about 6 to about 18 hours are often used. Preferably drying is accomplished using a nitrogen purge at about 100° C. for from about 6 to about 18 hours.

Although the above description is primarily in respect of chlorinating an organic feedstock comprising benzenes and/or chlorobenzene, it is expected that an organic feedstock comprising ortho-dichlorobenzene and/or meta-dichlorobenzene (irrespective of whether or not benzene and/or chlorobenzene is present) may be chlorinated in the presence of regenerated zeolite L to produce 1,2,4-trichlorobenzene wherein the regenerated zeolite L is zeolite L which has previously been used as catalyst for the catalytic chlorination of ortho-dichlorobenzene and/or meta-dichlorobenzene and which has thereafter been contacted with steam. It is further expected that steam treatment will enhance the production of 1,2,4-trichlorobenzene in comparison to the other isomers of trichlorobenzene produced. The chlorination conditions, proportions of steam treated zeolite L employed, and proportions of chlorinating agents used discussed above are satisfactory for the chlorination of ortho-dichlorobenzene and/or meta-dichlorobenzene. The above discussion in respect of the steam treatment of zeolite L and drying is also satisfactory. The reaction of benzene, chlorobenzene, meta-dichlorobenzene, ortho-dichlorobenzene, or a mixture of two or more thereof with chlorinating agent in the presence of a catalytic amount of zeolite L to produce 1,2,4-trichlorobenzene is discussed more fully in U.S. Pat. No. 4,835,327, the entire disclosure of which is incorporated herein by reference.

Accordingly, another embodiment of the invention is a process for regenerating zeolite L which has previously been used as catalyst for the catalytic chlorination of ortho-dichlorobenzene, meta-dichlorobenzene, or a mixture thereof, the process comprising contacting the zeolite L with steam.

Yet another embodiment of the invention is a process comprising reacting ortho-dichlorobenzene, meta-dichlorobenzene, or a mixture thereof initially present in an organic feedstock with chlorinating agent in the presence of regenerated zeolite L to produce an organic reaction product having an x-value greater than that of the organic feedstock, wherein the regenerated zeolite L is zeolite L which has previously been used as catalyst for the catalytic chlorination of ortho-dichlorobenzene, meta-dichlorobenzene, or a mixture thereof and which has thereafter been contacted with steam.

The invention is further described in conjunction with the following examples which are to be considered illustrative rather than limiting, and in which all parts are parts by weight and all percentages are percentages by weight unless otherwise specified.

In the Examples which follow, the reactor used for the continuous chlorination of monochlorobenzene and/or benzene comprised a pair of glass jacketed columns connected in series by a glass tee. Each column comprised an inner tube having a diameter of 25 millimeters and a length of 300 millimeters. Glass tees were attached to the top and bottom of the reactor. The bottom of the reactor was equipped with a poly(tetrafluoroethylene) bottom drip adapter. The temperature of the reactor jacket was controlled with a recirculating oil bath. Column temperature was monitored using a thermocouple connected to a digital temperature readout. The thermocouple sat in an Incoloy ® nickel alloy thermowell having an outside diameter of 6.35 millimeters. The zeolite L catalyst was supported on poly(tetrafluoroethylene) lab matting having 6.35 millimeter mesh openings. The matting was rolled tightly before being placed into the reactor. Organic reaction liquid from a surge pot was recirculated using a pump. After leaving the pump, the reaction liquid passed through a heat exchanger and then entered the bottom of the reactor. After passing through the reactor, the reaction liquid was removed from the top of the reactor and forwarded to the surge pot. In order to make flow velocity measurements, liquid leaving the top of the reactor could be diverted to a 250 milliliter addition funnel mounted atop the surge pot. Diversion was accomplished using a 9 millimeter three-way stopcock. One neck of the surge pot was used as an inlet for liquid received from the reactor, a second neck was fitted with a Claisen adapter atop which was the flow velocity measuring funnel and a loop sampling port, and a third neck was used as an outlet for gases. Gases leaving the surge pot through the third neck passed through a condenser maintained at about 30° C. Condensate was returned to the surge pot while uncondensed gases were passed through a 10 percent aqueous sodium hydroxide solution in a 19 liter carboy and then vented. Benzene was added to the reaction liquid recirculation loop through a tee located between the surge pot and the pump. Chlorine was introduced to the recirculating liquid through a tee located between the heat exchanger and the bottom of the reactor, and through the tee located at the midpoint of the reactor. The amounts of chlorine introduced through these tees were approximately equal. Overflow from the surge pot was removed though an outlet, passed through a liquid U-seal, and collected in a 500 milliliter receiver as product. In order to avoid entry of light, the entire system was wrapped with foil before chlorination was begun.

Zeolite L catalyst was charged to the reactor, half in each column. Monochlorobenzene was charged to the surge pot and the recirculation pump was started. Usually the recirculation pump was adjusted to provide a flow rate of about 450 milliliters/minute. The reactor was then brought up to about 10 Celsius degrees below the desired reaction temperature with nitrogen purging through the system. Chlorine introduction was then begun and brought to the desired rate. Loop samples were taken every two hours until the para-dichlorobenzene concentration reached 40 mole percent, at which time the introduction of benzene was begun and brought to the desired rate. Both loop and overflow samples were then taken at about 3-hour intervals. Operating times given in the Examples are referenced to the beginning of chlorine introduction.

Gas chromatographic analyses were performed on a Varian ® 3700 chromatograph with a flame ionization detector using a 3.175 millimeter diameter column 183 centimeters long of 3% SP-1000 stationary phase on 100/120 Supelcoport support (Supelco Inc.). The injection port temperature was set at 270° C. and the detector temperature was set at 320° C. Analyses were made in a programmable temperature mode with an initial temperature of 200° C. held for 12 minutes. The temperature was then increased at a programming rate of 6 Celsius degrees per minute.

The catalyst was originally prepared by the Zeochem subsidiary of United Catalysts, Inc. and was designated #L-2520. This catalyst, which comprised 80 percent by weight ELZ-L zeolite L powder from Union Carbide Corporation, 15 percent by weight L-90 fumed silica from Cabot Corporation, and 5 weight percent solids from Ludox ® colloidal sol from E.I. du Pont de Nemours & Co., Inc., was in the form of 3.175 millimeter diameter extrudates about 6 to about 10 millimeters long. Physical characteristics of the catalyst included a crush strength of 53.4 Newtons and a bulk density of 0.61 g/cm$^3$.

Reactivation of catalyst was accomplished by placing the used catalyst into one or two sections of a three section jacketed nickel reactor, connecting this nickel reactor at the top to a poly(tetrafluoroethylene)-lined pipe through which steam at a pressure of 483 kilopascals, gauge, entered the reactor and purged through the catalyst for 6 hours. Water, steam, and evolved materials were removed from the bottom of the reactor during this period. Drying of the reactivated catalyst was accomplished in the same nickel reactor. Overnight, nitrogen was introduced to the top of the reactor through a short length of poly(tetrafluoroethylene)-lined pipe, purged through the catalyst, and removed from the bottom of the reactor. During the nitrogen purge, steam at a pressure of 241 kilopascals, gauge, was applied to the jackets of the nickel reactor in order to heat the nitrogen and the catalyst and to thereby affect quicker catalyst drying.

The following is a key to abbreviations used in the Examples:

MCB = Monochlorobenzene
m-DCB = meta-Dichlorobenzene
p-DCB = para-Dichlorobenzene
o-DCB = ortho-Dichlorobenzene
TCB's = Trichlorobenzenes (all isomers)
Heavies = Polychlorinated cyclohexanes, polychlorinated cyclohexenes, and/or polychlorinated cyclohexadienes
Cumulative $Cl_2$ Utilization = 100 × (moles of chlorine atoms on the organic product − moles of chlorine atoms on the organic feedstock)/(total moles of $Cl_2$ fed)

EXAMPLE I

One hundred forty-five grams of deactivated zeolite L extrudates from several previous runs were mixed together and contacted with steam and dried according to the general procedure described above. The resulting dry reactivated zeolite L catalyst was charged to the chlorination reactor. Using the general procedure described above, the apparatus was charged with 10.311 moles of monochlorobenzene and then started up and operated at an average temperature of 90° C. while feeding 0.97 moles of chlorine per hour. After 8 hours benzene was introduced at an average rate of 0.51 moles/hour. The apparatus was operated continuously for 68 hours. Samples of product then being produced, that is, overflow from the surge pot, were collected after 15, 40, and 68 hours of operation. The compositions of these samples are summarized in Table 1.

TABLE 1

| | Sample Compositions | | |
|---|---|---|---|
| | Operating Time | | |
| | 15 hrs | 40 hrs | 68 hrs |
| Benzene, mole % | 4.74 | 4.47 | 4.09 |
| MCB, mole % | 39.10 | 30.02 | 28.80 |
| m-DCB, mole % | 0.55 | 0.64 | 0.65 |

TABLE 1-continued

| | Sample Compositions | | |
|---|---|---|---|
| | Operating Time | | |
| | 15 hrs | 40 hrs | 68 hrs |
| p-DCB, mole % | 48.14 | 55.37 | 55.40 |
| o-DCB, mole % | 6.98 | 8.75 | 9.21 |
| TCB's, mole % | 0.32 | 0.47 | 0.58 |
| Heavies, mole % | 0.15 | 0.22 | 0.29 |
| x-value | 1.52 | 1.61 | 1.63 |
| P/O Ratio | 6.90 | 6.33 | 6.02 |
| Cumulative $Cl_2$ Utilization, % | 70.02 | 73.70 | 73.50 |

EXAMPLE II

One hundred ten grams of the zeolite L extrudates removed from the apparatus following Example I were contacted with steam and dried according to the general procedure described above. The resulting dry reactivated zeolite L catalyst was charged to the chlorination reactor. Using the general procedure described above, the apparatus was charged with 10.377 moles of monochlorobenzene and then started up and operated at an average temperature of 90° C. while feeding 0.726 moles of chlorine per hour. After 9 hours benzene was introduced at an average rate of 0.38 moles/hour. The apparatus was operated continuously for 91 hours. Samples of product then being produced were collected after 16, 41, 68, and 91 hours of operation. The compositions of these samples are summarized in Table 2.

TABLE 2

| | Sample Compositions | | | |
|---|---|---|---|---|
| | Operating Time | | | |
| | 16 hrs | 41 hrs | 68 hrs | 91 hrs |
| Benzene, mole % | 3.56 | 4.32 | 4.56 | 4.36 |
| MCB, mole % | 40.33 | 34.21 | 36.40 | 26.73 |
| m-DCB, mole % | 0.50 | 0.53 | 0.54 | 0.58 |
| p-DCB, mole % | 49.61 | 53.91 | 51.11 | 59.34 |
| o-DCB, mole % | 5.87 | 6.77 | 7.07 | 8.59 |
| TCB's, mole % | 0.11 | 0.21 | 0.27 | 0.37 |
| Heavies, mole % | 0.02 | 0.06 | 0.06 | 0.06 |
| x-value | 1.53 | 1.57 | 1.55 | 1.65 |
| P/O Ratio | 8.45 | 7.96 | 7.23 | 6.91 |
| Cumulative $Cl_2$ Utilization, % | 75.26 | 75.45 | 74.64 | 73.68 |

EXAMPLE III

Ninety-one grams of the zeolite L extrudates removed from the apparatus following Example II were contacted with steam and dried according to the general procedure described above. The resulting dry reactivated zeolite L catalyst was charged to the chlorination reactor. Using the general procedure described above, the apparatus was charged with 10.898 moles of monochlorobenzene and then started up and operated at an average temperature of 90° C. while feeding 0.602 moles of chlorine per hour. After 10 hours benzene was introduced at an average rate of 0.39 moles/hour. The apparatus was operated continuously for 105 hours. Samples of product then being produced were collected after 16, 41, 68, and 92 hours of operation. The compositions of these samples are summarized in Table 3.

TABLE 3

| | Sample Compositions | | | |
|---|---|---|---|---|
| | Operating Time | | | |
| | 16 hrs | 41 hrs | 68 hrs | 92 hrs |
| Benzene, mole % | 4.91 | 4.10 | 5.13 | 4.63 |
| MCB, mole % | 39.80 | 36.30 | 36.64 | 28.55 |
| m-DCB, mole % | 0.45 | 0.49 | 0.49 | 0.55 |
| p-DCB, mole % | 48.70 | 51.83 | 49.94 | 56.43 |
| o-DCB, mole % | 6.03 | 7.07 | 7.50 | 9.26 |
| TCB's, mole % | 0.11 | 0.19 | 0.27 | 0.53 |
| Heavies, mole % | 0.00 | 0.01 | 0.03 | 0.05 |
| x-value | 1.50 | 1.56 | 1.53 | 1.63 |
| P/O Ratio | 8.08 | 7.33 | 6.66 | 6.09 |
| Cumulative $Cl_2$ Utilization, % | 84.76 | 79.92 | 80.74 | 68.77 |

Examples I, II, and III show that although the P/O Ratio decreases as zeolite L catalyst is used, nevertheless the zeolite L catalyst may be reactivated by the steam treatment of the invention. The data of these Examples also show that the steam treatment improves the chlorine utilization.

Although the present invention has been described with reference to specific details of certain embodiments thereof, it is not intended that such details should be regarded as limitations upon the scope of the invention except insofar as they are included in the accompaning claims.

I claim:

1. A process for reactivating zeolite L which has previously been used as catalyst for the catalytic chlorination of benzene, chlorobenzene, or a mixture thereof, said process comprising contacting said zeolite L with steam.

2. The process of claim 1 wherein the pressure of said steam is above ambient atmospheric pressure.

3. The process of claim 1 wherein the pressure of said steam is at least about 130 kilopascals, gauge.

4. The process of claim 1 wherein the pressure of said steam is in the range of from about 130 to about 1100 kilopascals, gauge.

5. The process of claim 1 wherein said zeolite L is contacted with said steam for at least one hour.

6. The process of claim 1 wherein said zeolite L is contacted with said steam for a period in the range of from about 3 hours to about 24 hours.

7. A process for regenerating zeolite L which has previously been used as catalyst for the catalytic chlorination of ortho-dichlorobenzene, meta-dichlorobenzene, or a mixture thereof, said process comprising contacting said zeolite L with steam.

8. The process of claim 7 wherein the pressure of said steam is above ambient atmospheric pressure.

9. The process of claim 7 wherein the pressure of said steam is at least about 130 kilopascals, gauge.

10. The process of claim 7 wherein the pressure of said steam is in the range of from about 130 to about 1100 kilopascals, gauge.

11. The process of claim 7 wherein said zeolite L is contacted with said steam for at least one hour.

12. The process of claim 7 wherein said zeolite L is contacted with said steam for a period in the range of from about 3 hours to about 24 hours.

* * * * *